US012642532B2

(12) United States Patent
Wang et al.

(10) Patent No.: US 12,642,532 B2
(45) Date of Patent: Jun. 2, 2026

(54) MEDICAL DEVICE SYSTEM FOR OCCLUDING A LEFT ATRIAL APPENDAGE AND IMPLANT REMODELING TOOL

(71) Applicant: BOSTON SCIENTIFIC SCIMED, INC., Maple Grove, MN (US)

(72) Inventors: Jerry Wang, Edina, MN (US); James M. Anderson, Corcoran, MN (US); Joshua Mark Inouye, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 302 days.

(21) Appl. No.: 18/375,766

(22) Filed: Oct. 2, 2023

(65) Prior Publication Data

US 2024/0108353 A1 Apr. 4, 2024

Related U.S. Application Data

(60) Provisional application No. 63/412,629, filed on Oct. 3, 2022.

(51) Int. Cl.
*A61B 17/12* (2006.01)
*A61B 17/00* (2006.01)

(52) U.S. Cl.
CPC ................... *A61B 17/12122* (2013.01); *A61B 2017/00632* (2013.01); *A61B 2217/002* (2013.01); *A61B 2560/04* (2013.01)

(58) Field of Classification Search
CPC .... A61B 17/12122; A61B 2017/00632; A61B 2217/002; A61B 2560/04; A61B 2017/00893; A61B 2017/00955; A61B 2090/3966; A61B 2017/12095; A61B 17/12172; A61B 17/12177
See application file for complete search history.

(56) References Cited

U.S. PATENT DOCUMENTS

| | | | |
|---|---|---|---|
| 9,901,350 B2 | 2/2018 | McGuckin, Jr. | |
| 11,191,546 B2 | 12/2021 | Gong et al. | |
| 2001/0041914 A1 * | 11/2001 | Frazier ............... | A61B 17/0057 606/225 |
| 2019/0336132 A1 | 11/2019 | Warner et al. | |
| 2022/0031333 A1 | 2/2022 | Zhou et al. | |
| 2022/0054117 A1 | 2/2022 | Rafiee et al. | |
| 2022/0079667 A1 | 3/2022 | Gabay et al. | |

* cited by examiner

*Primary Examiner* — Richard G Louis
(74) *Attorney, Agent, or Firm* — Seager, Tufte & Wickhem LLP

(57) ABSTRACT

A medical device system may include an occlusive implant including a central hub and a plurality of elongate members configured to shift between extended and radially expanded configurations. The central hub includes a plurality of conduits extending from a proximal end to a radially outward facing surface. The plurality of elongate members is configured to extend through the conduits in the radially expanded configuration. An implant remodeling tool may include an elongate sheath having at least one lumen, a plunger guide, and a plurality of plunger shafts extending from the at least one lumen through the plunger guide. The plunger guide is configured to direct the plunger shafts radially outward as the plunger shafts are advanced distally. The plunger shafts are configured to engage a medical implant and urge at least a portion of the implant radially outward.

8 Claims, 15 Drawing Sheets

MEDICAL DEVICE SYSTEM FOR OCCLUDING A LEFT ATRIAL APPENDAGE AND IMPLANT REMODELING TOOL

CROSS REFERENCE TO RELATED APPLICATIONS

This application claims the benefit of priority of U.S. Provisional Application No. 63/412,629 filed Oct. 3, 2022, the entire disclosure of which is hereby incorporated by reference.

TECHNICAL FIELD

The present disclosure pertains to medical devices and systems, and methods for manufacturing and using medical devices and systems. More particularly, the present disclosure pertains to medical implants for occluding a left atrial appendage and/or implant remodeling tools configured to improve engagement of a medical implant with adjacent tissue.

BACKGROUND

Diseases and/or medical conditions that impact the cardiovascular system are prevalent throughout the world. Traditionally, treatment of the cardiovascular system was often conducted by directly accessing the impacted part of the system. More recently, less invasive therapies have been developed, and have gained wide acceptance among patients and clinicians.

Atrial fibrillation is a common sustained cardiac arrhythmia affecting over 30 million people worldwide, according to some estimates. Atrial fibrillation is the irregular, chaotic beating of the upper chambers of the heart. Electrical impulses discharge so rapidly that the atrial muscle quivers or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

The disclosure relates to medical implants for occluding the left atrial appendage and/or implant remodeling tools configured to improve engagement of a medical implant with adjacent tissue. Of the known medical devices, systems, and methods, each has certain advantages and disadvantages. There is an ongoing need to provide alternative medical devices and systems, as well as alternative methods for manufacturing and using medical devices and systems.

SUMMARY

In one example, a medical device system for occluding a left atrial appendage may comprise an occlusive implant including a central hub and a plurality of elongate members configured to shift between an extended configuration and a radially expanded configuration. The central hub may include a plurality of conduits extending from a proximal end of the central hub to a radially outward facing surface of the central hub. The plurality of elongate members may be configured to extend through the plurality of conduits in the radially expanded configuration.

In addition or alternatively to any example disclosed herein, axial movement of the plurality of elongate members in a distal direction is configured to shift the plurality of elongate members from the extended configuration to the radially expanded configuration.

In addition or alternatively to any example disclosed herein, the plurality of elongate members is self-biased toward the radially expanded configuration.

In addition or alternatively to any example disclosed herein, the plurality of conduits directs the plurality of elongate members radially outward from the central hub as proximal ends of the plurality of elongate members move closer to the proximal end of the central hub.

In addition or alternatively to any example disclosed herein, distal ends of the plurality of elongate members are fixedly attached to the central hub proximate a distal end of the central hub.

In addition or alternatively to any example disclosed herein, a portion of each elongate member of the plurality of elongate members is oriented generally parallel with the radially outward facing surface of the central hub in the extended configuration.

In addition or alternatively to any example disclosed herein, the portion of each elongate member of the plurality of elongate members that is oriented generally parallel with the radially outward facing surface of the central hub in the extended configuration is oriented non-parallel with the radially outward facing surface of the central hub in the radially expanded configuration.

In addition or alternatively to any example disclosed herein, the portion of each elongate member of the plurality of elongate members that is oriented generally parallel with the radially outward facing surface of the central hub in the extended configuration is disposed between the proximal end of the central hub and a distal end of the central hub.

In addition or alternatively to any example disclosed herein, the medical device system may further comprise a delivery sheath having a lumen extending therein, wherein the occlusive implant is disposed within the lumen with the plurality of elongate members in the extended configuration during delivery to the left atrial appendage.

In addition or alternatively to any example disclosed herein, moving the occlusive implant outside of the lumen permits the plurality of elongate members to shift from the extended configuration to the radially expanded configuration.

In addition or alternatively to any example disclosed herein, the plurality of elongate members is configured to shift from the extended configuration to the radially expanded configuration simultaneously.

In addition or alternatively to any example disclosed herein, the plurality of elongate members is configured to shift from the extended configuration to the radially expanded configuration individually.

In addition or alternatively to any example disclosed herein, an implant remodeling tool configured to improve engagement of a medical implant with adjacent tissue may comprise an elongate sheath having at least one lumen extending therein, and a plunger guide disposed proximate a distal end of the elongate sheath; and a plurality of plunger shafts extending from the at least one lumen through the plunger guide. The plunger guide may be configured to direct the plurality of plunger shafts radially outward from the plunger guide as the plurality of plunger shafts is advanced distally. The plurality of plunger shafts may be configured to engage the medical implant and urge at least a portion of the medical implant radially outward from the elongate sheath.

In addition or alternatively to any example disclosed herein, at least one plunger shaft of the plurality of plunger shafts includes an implant interface element at a distalmost end thereof.

In addition or alternatively to any example disclosed herein, each plunger shaft of the plurality of plunger shafts is engaged with a compression spring.

In addition or alternatively to any example disclosed herein, each plunger shaft of the plurality of plunger shafts is engaged with its own compression spring.

In addition or alternatively to any example disclosed herein, the elongate sheath includes a main plunger shaft disposed within the at least one lumen. Each plunger shaft of the plurality of plunger shafts may be operably engaged with the main plunger shaft.

In addition or alternatively to any example disclosed herein, each plunger shaft of the plurality of plunger shafts is axially translatable independently of each other.

In addition or alternatively to any example disclosed herein, at least one plunger shaft of the plurality of plunger shafts is steerable independently of any other plunger shafts of the plurality of plunger shafts.

In addition or alternatively to any example disclosed herein, a kit may comprise a delivery sheath configured to deploy a medical implant at a treatment site, wherein the medical implant is configured to shift from a delivery configuration toward a deployed configuration upon release from the delivery sheath; and an implant remodeling tool configured to improve engagement of the medical implant with adjacent tissue at the treatment site. The implant remodeling tool may include an elongate sheath having at least one lumen extending therein, and a plunger guide disposed proximate a distal end of the elongate sheath; and a plurality of plunger shafts extending from the at least one lumen through the plunger guide. The plunger guide may be configured to direct the plurality of plunger shafts radially outward from the plunger guide as the plurality of plunger shafts is advanced distally. The plurality of plunger shafts may be configured to engage the medical implant and urge at least a portion of the medical implant radially outward from the elongate sheath and into engagement with adjacent tissue at the treatment site.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figures 1, 2:
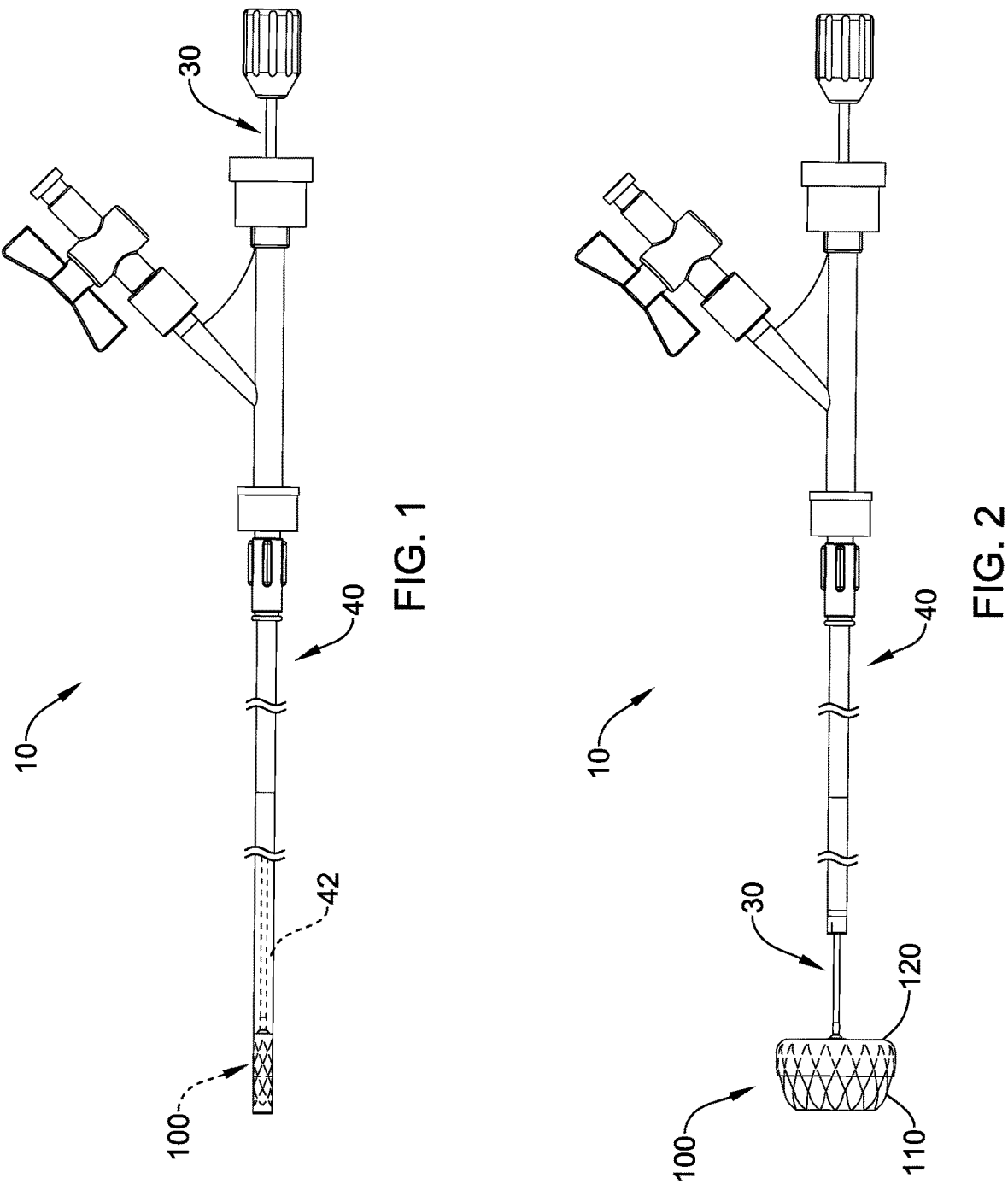
FIGS. 1-2 are side views of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. It shall be understood that the discussion(s) herein may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean the maximum outer dimension, "radial extent" may be understood to mean the maximum radial dimension, "longitudinal extent" may be understood to mean the maximum longitudinal dimension, etc. Each instance of an "extent" may be different (e.g., axial, longitudinal, lateral, radial, circumferential, etc.) and will be apparent to the skilled person from the context of the individual usage. In some instances, an "extent" may be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of medical implants, systems, and methods of manufacturing the same. It should be noted that in any given figure, some features of the medical implants, systems, and methods may not be shown, or may be shown schematically, for simplicity. Additional details regarding some elements may be illustrated in other figures in greater detail. The devices and/or methods disclosed herein may provide a number of desirable features and benefits as described in more detail below.

FIGS. 1-2 schematically illustrate selected components and/or arrangements of a medical device system 10 for occluding a left atrial appendage. The medical device system 10 may be used to deliver and/or deploy a variety of medical implants (e.g., a cardiovascular medical implant, an occlusive medical implant, etc.) to one or more locations within the anatomy of a patient including but not limited to the heart and/or the vasculature.

The medical device system 10 may include a delivery sheath 40 having a lumen 42 extending from a proximal opening to a distal opening, a core wire 30 movably and/or slidably disposed within the lumen 42, and a medical implant 100. The medical implant 100 may be configured to occlude the left atrial appendage of the patient. In some embodiments, other medical implants may be used in place of the medical implant 100.

The medical implant 100 may include an expandable scaffold 110 configured to shift between a delivery configuration (e.g., FIG. 1), wherein the medical implant 100 is disposed within the lumen 42 proximate the distal opening in the delivery configuration, and a deployed configuration (e.g., FIG. 2), wherein the medical implant 100 and/or the expandable scaffold 110 is configured to shift between the delivery configuration and the deployed configuration when the medical implant 100 is disposed distal of the distal opening of the lumen 42 and/or the delivery sheath 40, and/or when the medical implant 100 is unconstrained by the delivery sheath 40. The medical implant 100 may include a covering 120.

The medical implant 100 may be disposed at and/or releasably connected to a distal portion of the core wire 30. In some embodiments, the medical implant 100 may be releasably connected to the distal end of the core wire 30. The core wire 30 may be slidably and/or rotatably disposed within the lumen 42 of the delivery sheath 40. In some embodiments, a proximal end of the core wire 30 may extend proximally of a proximal end of the delivery sheath 40 and/or the proximal opening of the lumen 42 for manual manipulation by a clinician or practitioner.

Some suitable, but non-limiting, examples of materials for the medical device system 10, the core wire 30, the delivery sheath 40, and/or the medical implant 100, etc. are discussed below. It is contemplated that any and/or all implants disclosed herein may be used in accordance with and/or be associated with the medical device system 10 described above.

Figure 3:
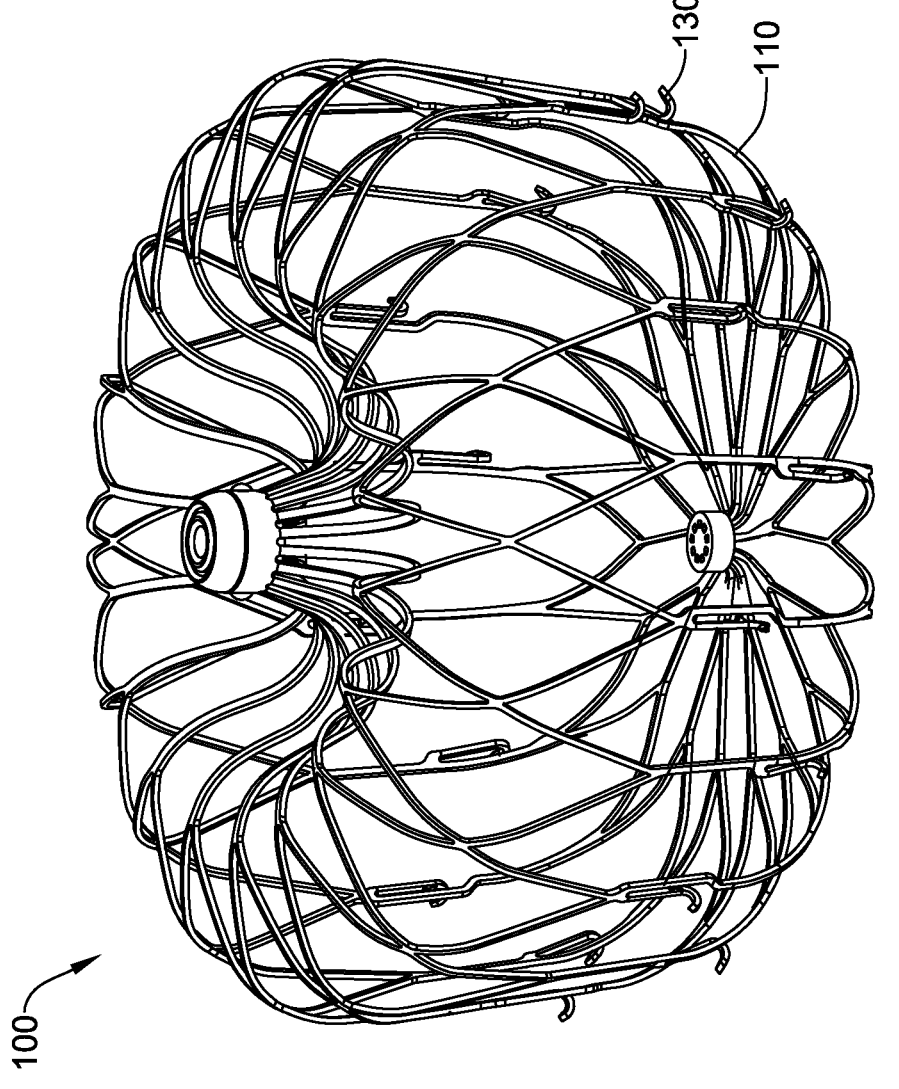
FIG. 3 is a perspective view of a prior art configuration of a medical implant.

FIG. 3 illustrates selected aspects of the medical implant 100, which may be known in the art. The medical implant 100 may include a plurality of anchor members 130 extending outward from the expandable scaffold 110. The expandable scaffold 110 may extend from a proximal end to a distal end in a continuous and interconnected manner. The expandable scaffold may be a single monolithic structure. The struts of the expandable scaffold 110 may be fixedly connected at the proximal end and at the distal end.

Figure 4:
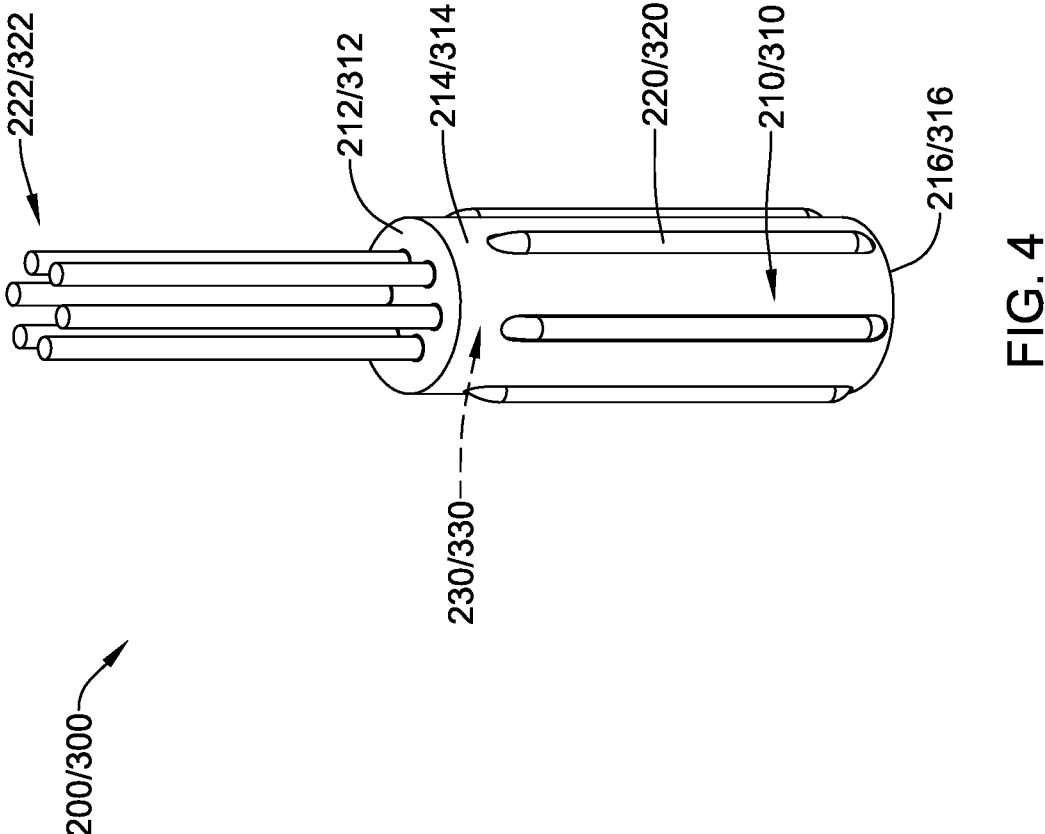
FIG. 4 illustrates selected aspects of an occlusive implant having a plurality of elongate members in an extended configuration.
Figures 5, 6:
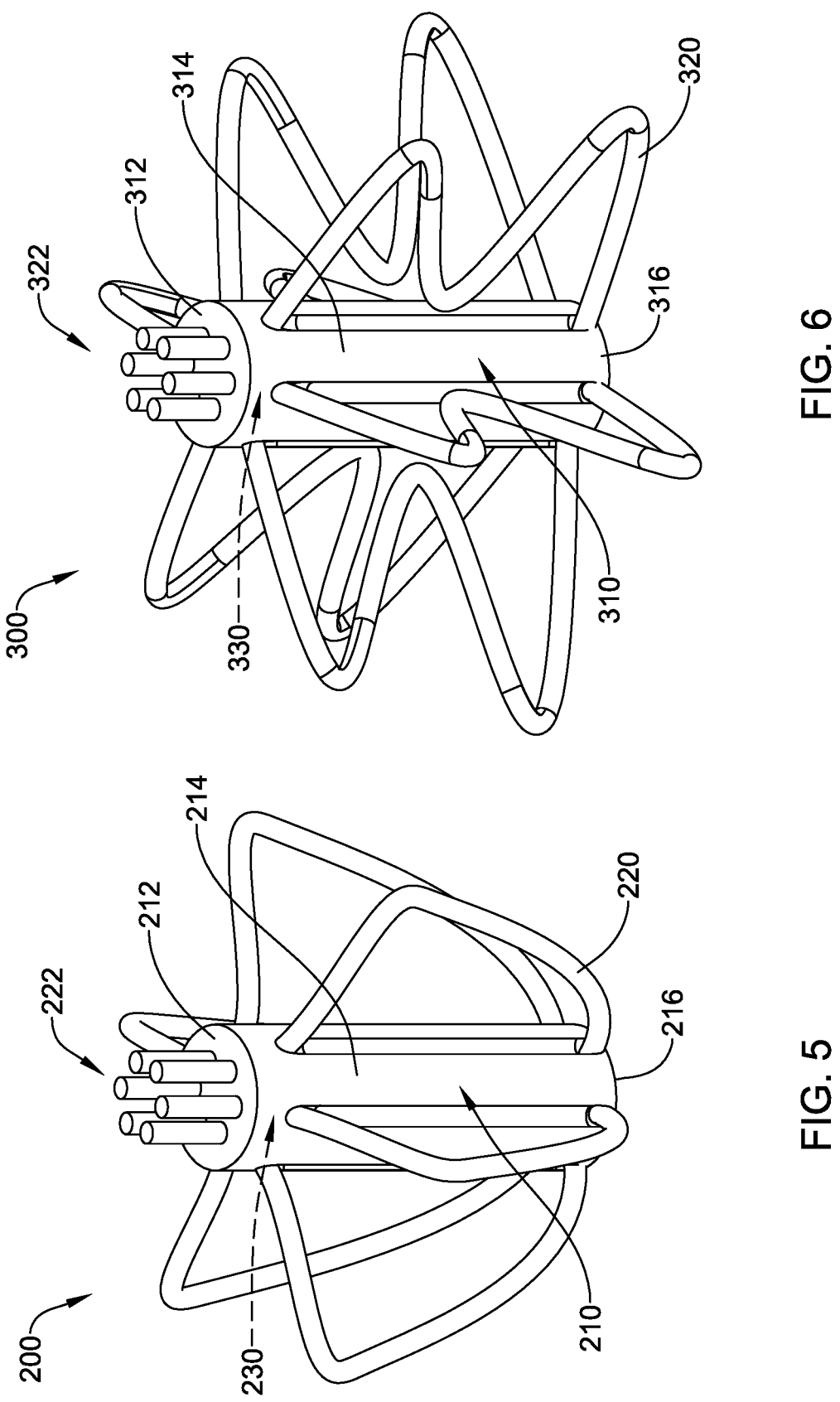
FIG. 5 illustrates selected aspects of the occlusive implant of FIG. 4 with the plurality of elongate members in a radially expanded configuration.
FIG. 6 illustrates selected aspects of the occlusive implant of FIG. 4 with the plurality of elongate members in a radially expanded configuration.

FIGS. 4-6 illustrates example configurations of an occlusive implant 200/300 according to the disclosure. The occlusive implant 200/300 may be used in place of the medical implant 100 in the medical device system 10. The occlusive implant 200/300 may be disposable at and/or releasably connectable to the distal portion of the core wire 30. In some embodiments, the occlusive implant 200/300 may include a threaded connector configured to engage a mating threaded connector on the core wire 30. Other means of connecting the occlusive implant 200/300 to the core wire 30 are also contemplated.

The occlusive implant 200/300 may include a central hub 210/310 and a plurality of elongate members 220/320 configured to shift between an extended configuration (e.g., FIG. 4) and a radially expanded configuration (e.g., FIGS. 5-6). The central hub 210/310 may include a plurality of conduits 230/330 extending from a proximal end 212/312 of the central hub 210/310 to a radially outward facing surface 214/314 of the central hub 210/310. In at least some embodiments, the plurality of elongate members 220/320 may be configured to extend through the plurality of conduits 230/330 in the radially expanded configuration.

In some embodiments, proximal ends 222/322 of the plurality of elongate members 220/320 may be axially and/or longitudinally spaced apart from the central hub 210/310 and/or the proximal end 212/312 of the central hub 210/310 in the extended configuration. For example, the proximal ends 222/322 of the plurality of elongate members 220/320 may be axially and/or longitudinally spaced apart proximally from the central hub 210/310 and/or the proximal end 212/312 of the central hub 210/310 in the extended configuration.

In some embodiments, when the plurality of elongate members 220/320 is in the extended configuration, axial movement of proximal ends 222/322 of the plurality of elongate members 220/320 in a distal direction relative to the central hub 210/310 and/or the proximal end 212/312 of the central hub 210/310 may be configured to shift the plurality of elongate members 220/320 from the extended configuration toward and/or to the radially expanded configuration. In some embodiments, the plurality of elongate members 220/320 may be self-biased toward the radially expanded configuration. In some embodiments, the plurality of elongate members 220/320 may be self-biased toward the radially expanded configuration when the plurality of elongate members 220/320 is unconstrained. For example, the delivery sheath 40 may be configured to constrain the plurality of elongate members 220/320 in the extended configuration when the occlusive implant 200/300 is disposed within the lumen 42 of the delivery sheath 40. In another example, the plurality of elongate members 220/320 may be constrained in the extended configuration by friction, tension, or another holding force. In some embodiments, moving the occlusive implant 200/300 outside of the lumen 42 of the delivery sheath 40 may permit the plurality of elongate members 220/320 to shift from the extended configuration toward and/or to the radially expanded configuration.

In some embodiments, the plurality of conduits 230/330 may be configured to direct the plurality of elongate members 220/320 radially outward from the central hub 210/310 and/or the radially outward facing surface 214/314 of the central hub 210/310 as the proximal ends 222 of the plurality of elongate members 220/320 move closer to the proximal end 212/312 of the central hub 210/310. In some embodiments, distal ends of the plurality of elongate members 220/320 may be fixedly attached to the central hub 210/310 proximate a distal end 216/316 of the central hub 210/310.

In some embodiments, a portion of each elongate member of the plurality of elongate members 220/320 may be oriented generally parallel with the radially outward facing surface 214/314 of the central hub 210/310 in the extended configuration. In some embodiments, the portion of each elongate member of the plurality of elongate members 220/320 that is oriented generally parallel with the radially outward facing surface 214/314 of the central hub 210/310 in the extended configuration may be oriented non-parallel with the radially outward facing surface 214/314 of the central hub 210/310 in the radially expanded configuration. In at least some embodiments, the portion of each elongate member of the plurality of elongate members 220/320 that is oriented generally parallel with the radially outward facing surface 214/314 of the central hub 210/310 in the extended configuration may be disposed between the proximal end 212/312 of the central hub 210/310 and the distal end 216/316 of the central hub 210/310.

In some embodiments, the plurality of elongate members 220/320 may be configured to shift from the extended configuration (e.g., FIG. 4) toward and/or to the radially expanded configuration (e.g., FIGS. 5-6) simultaneously. In some embodiments, the plurality of elongate members 220/320 may be configured to shift from the extended configuration (e.g., FIG. 4) toward and/or to the radially expanded configuration (e.g., FIGS. 5-6) individually (e.g., one at a time). In some embodiments, two or more elongate members or a first group of elongate members of the plurality of elongate members 220/320 may be configured to shift from the extended configuration (e.g., FIG. 4) toward and/or to the radially expanded configuration (e.g., FIGS. 5-6) simultaneously, while other elongate members or a second group or other groups of the plurality of elongate members 220/320 may be configured to shift from the extended configuration (e.g., FIG. 4) toward and/or to the radially expanded configuration (e.g., FIGS. 5-6) separately from the two or more elongate members or the first group of elongate members of the plurality of elongate members 220/320. Other configurations are also contemplated.

In some embodiments, the plurality of elongate members 220/320 may be at least partially steerable. In some embodiments, at least one elongate member of the plurality of elongate members 220/320 may be at least partially steerable independently of any other elongate member of the plurality of elongate members 220/320. Steerability of the plurality of elongate members 220/320 may permit non-planar extension of the plurality of elongate members 220/320 (e.g., at least one elongate member of the plurality of elongate members 220/320 may be skewed and/or out of plane with respect to a remainder of the plurality of elongate members 220/320) when shifting toward and/or to the radially expanded configuration. Flexibility and/or steerability of movement of the plurality of elongate members 220/320 may permit the occlusive implant 200/300 to better close off an irregular opening into a body cavity and/or a body lumen, and/or to better close off a body cavity and/or a body lumen that is irregularly shaped.

Figure 7:
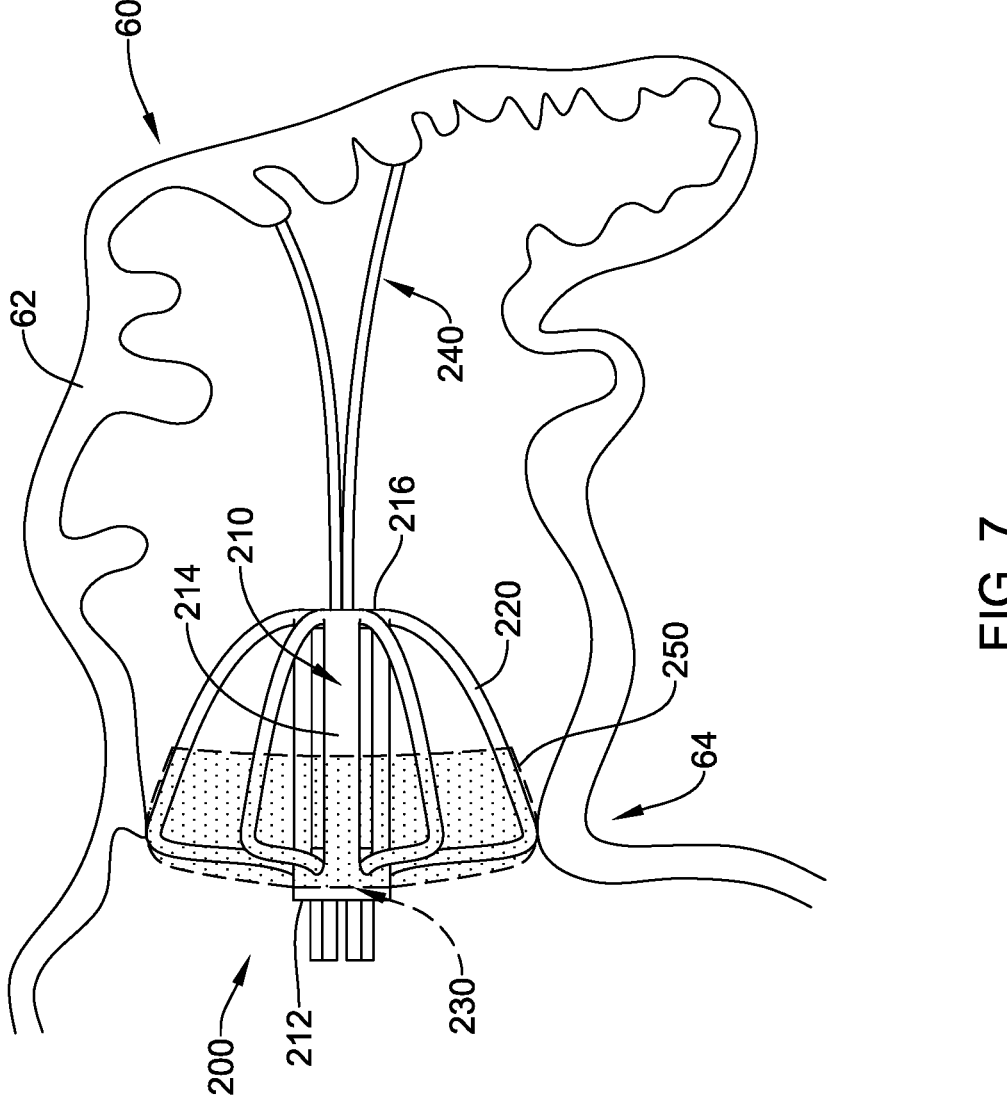
FIG. 7 illustrates selected aspects of the occlusive implant of FIG. 5 disposed within a left atrial appendage.

FIG. 7 illustrates the occlusive implant 200 disposed within a left atrial appendage 60 after delivery thereto and/or after deployment therein. As shown, the left atrial appendage 60 may include a wall 62. In some embodiments, the wall 62 of the left atrial appendage 60 may have an irregular thickness and/or shape. The left atrial appendage 60 may open into the left atrium of the heart of the patient at the ostium 64. The plurality of elongate members 220 may be positioned adjacent the ostium 64 in the radially expanded configuration. In some embodiments, the plurality of elongate members 220 may be configured to shift radially outward from the central hub 210 to form a generally bulbous shape in the radially expanded configuration.

In some embodiments, the occlusive implant 200 may include one or more anchoring tethers 240 extending distally from the central hub 210 and/or the plurality of elongate members 220 deeper into the left atrial appendage 60. The one or more anchoring tethers 240 may engage the wall 62 of the left atrial appendage 60 and provide an anchoring point for the occlusive implant 200. In some embodiments, the occlusive implant 200 may optionally include an occlusive element 250 disposed along an outer surface of the plurality of elongate members 220. The occlusive element 250 may aid in separating the left atrial appendage 60 from the left atrium of the heart and/or in effectively removing the left atrial appendage 60 from the patient's circulatory system. In some embodiments, the occlusive implant 200 may include a plurality of anchor members extending radially outward from the plurality of elongate members 220 and configured to engage the wall 62 of the left atrial appendage 60 proximate the plurality of elongate members 220. In some embodiments, at least some of the plurality of anchor members may extend through the occlusive element 250 before engaging the wall 62 of the left atrial appendage 60. Other configurations are also contemplated.

Figure 8:
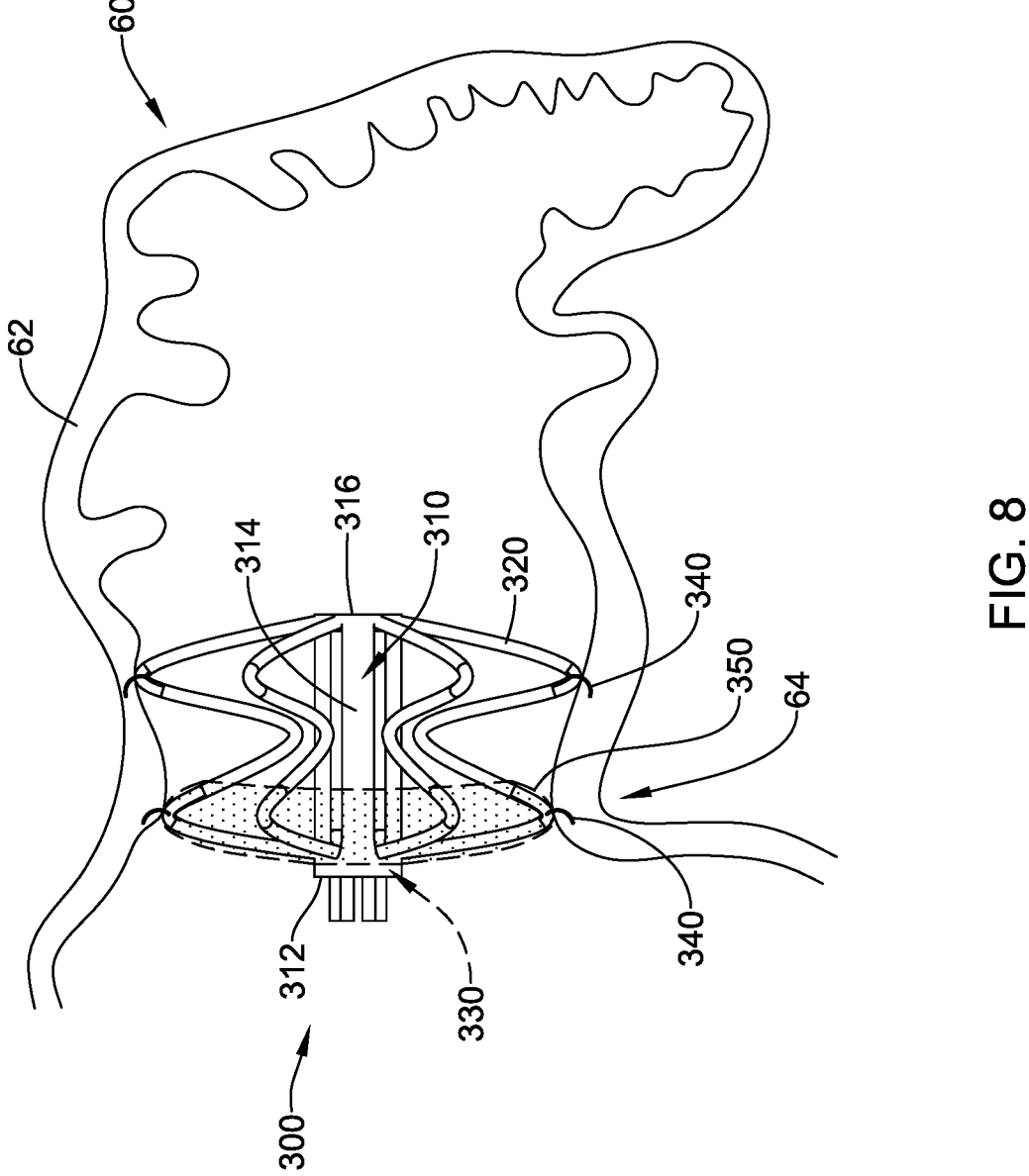
FIG. 8 illustrates selected aspects of the occlusive implant of FIG. 6 disposed within a left atrial appendage.
Figure 9:
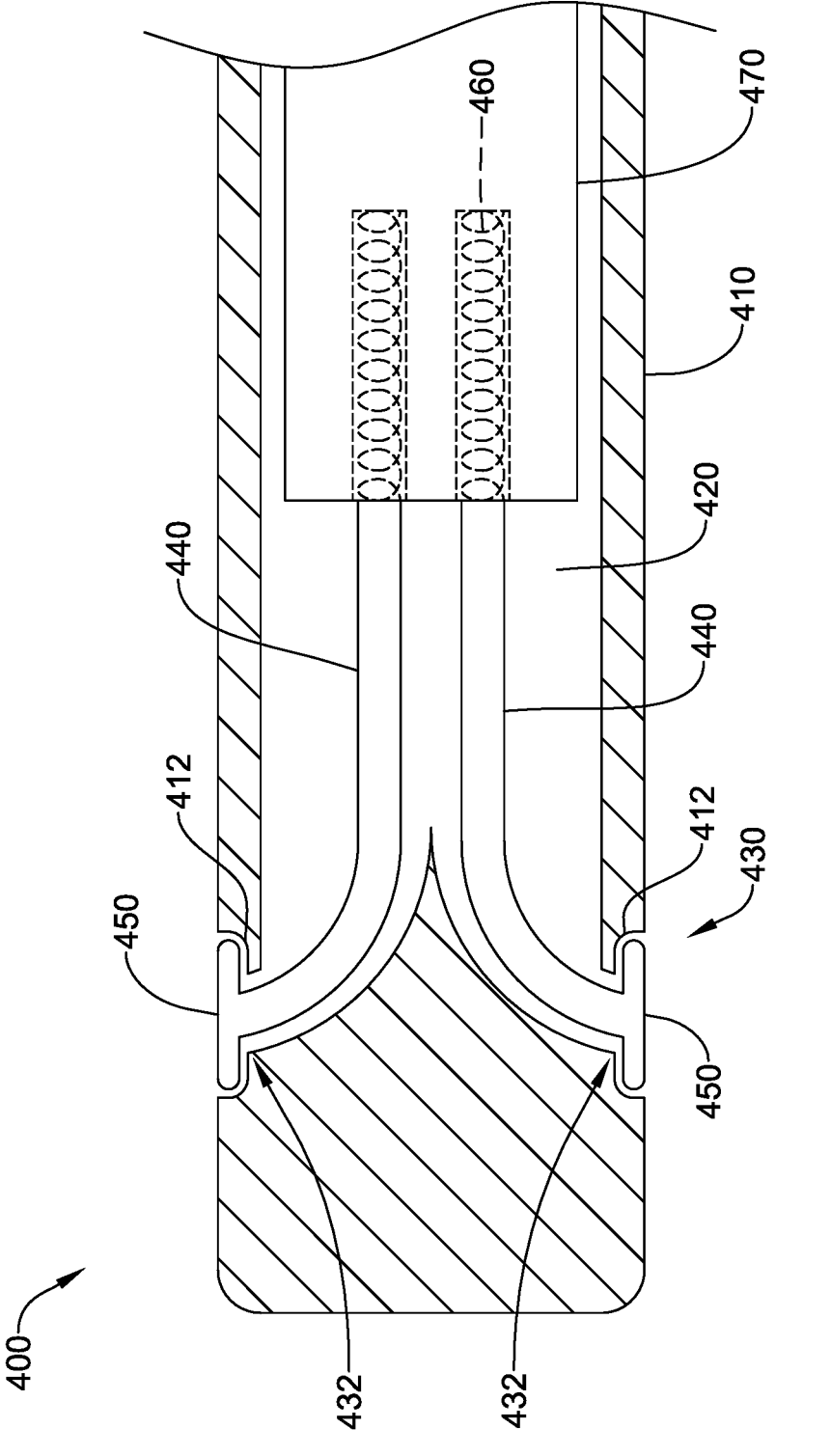
FIGS. 9-13 illustrate selected aspects of an implant remodeling tool.

FIG. 8 illustrates the occlusive implant 300 disposed within a left atrial appendage 60 after delivery thereto and/or after deployment therein. The plurality of elongate members 320 may be positioned adjacent the ostium 64 in the radially expanded configuration. In some embodiments, the plurality of elongate members 320 may be configured to shift radially outward from the central hub 310 to form a zigzag shape and/or a multi-lobed structure in the radially expanded configuration.

In some embodiments, the occlusive implant 300 may include one or more anchoring tethers extending distally from the central hub 310 and/or the plurality of elongate members 220 deeper into the left atrial appendage 60. The one or more anchoring tethers may engage the wall 62 of the left atrial appendage 60 and provide an anchoring point for the occlusive implant 300. In some embodiments, the occlusive implant 300 may optionally include an occlusive element 350 disposed along an outer surface of the plurality of elongate members 320. The occlusive element 350 may aid in separating the left atrial appendage 60 from the left atrium of the heart and/or in effectively removing the left atrial appendage 60 from the patient's circulatory system. In some embodiments, the occlusive implant 300 may include a plurality of anchor members 340 extending radially outward from the plurality of elongate members 320 and configured to engage the wall 62 of the left atrial appendage 60 proximate the plurality of elongate members 320. In some embodiments, the plurality of anchor members 340 may extend radially outward from tips of zigzags in the zigzag shape and/or from tips of lobes in the multi-lobed structure. In some embodiments, at least some of the plurality of anchor members 340 may extend through the occlusive element 350 before engaging the wall 62 of the left atrial appendage 60. Other configurations are also contemplated.

Other shapes and/or configurations for the plurality of elongate members 220/320 of the occlusive implant 200/300 are also contemplated. For example, when viewed from the side of the occlusive implant 200/300, the plurality of elongate members 220/320 may have a D-shape, a B-shape, a P-shape, an E-shape, or other regular and/or irregular shapes that may enhance engagement of the plurality of elongate members 220/320 and/or the plurality of anchor members with the wall 62 of the left atrial appendage 60.

FIGS. 9-13 illustrate selected aspects of an implant remodeling tool 400 configured to improve engagement of a medical implant with adjacent tissue. When some medical implants (e.g., an occlusive implant, a replacement heart valve, a stent, etc.) are deployed, the surrounding tissue may be uneven and/or irregular resulting in portions of the medical implant being in poor apposition to the tissue. In order to improve anchoring, sealing, and/or overall function of the medical implants, the implant remodeling tool 400 may be used to urge portions of the medical implant into better apposition with the surrounding tissue.

The implant remodeling tool 400 may include an elongate sheath 410 having at least one lumen 420 extending therein. In some embodiments, the elongate sheath 410 may be an elongate shaft, a tubular member, a hypotube, etc. The implant remodeling tool 400 may include a plunger guide 430 disposed proximate a distal end of the elongate sheath 410. The implant remodeling tool 400 may include a plurality of plunger shafts 440 extending from the at least one lumen 420 through the plunger guide 430. In some embodiments, the plurality of plunger shafts 440 may all be disposed within a single lumen. In some embodiments, each plunger shaft of the plurality of plunger shafts 440 may be disposed in its own lumen. Other configurations, including combinations thereof, are also contemplated.

In some embodiments, the plurality of plunger shafts 440 may vary in physical properties proximally to distally. In some embodiments, one plunger shaft of the plurality of plunger shafts 440 may vary in physical properties proximally to distally. In some embodiments, multiple plunger shafts of the plurality of plunger shafts 440 may vary in physical properties proximally to distally. In some embodiments, each plunger shaft of the plurality of plunger shafts 440 may vary in physical properties proximally to distally. In some embodiments, the physical properties that may vary may include flexibility, pushability, column strength, bendability, steerability, etc. The physical properties may be varied proximally to distally to accommodate needs and/or features of the patient's anatomy.

Figure 10:
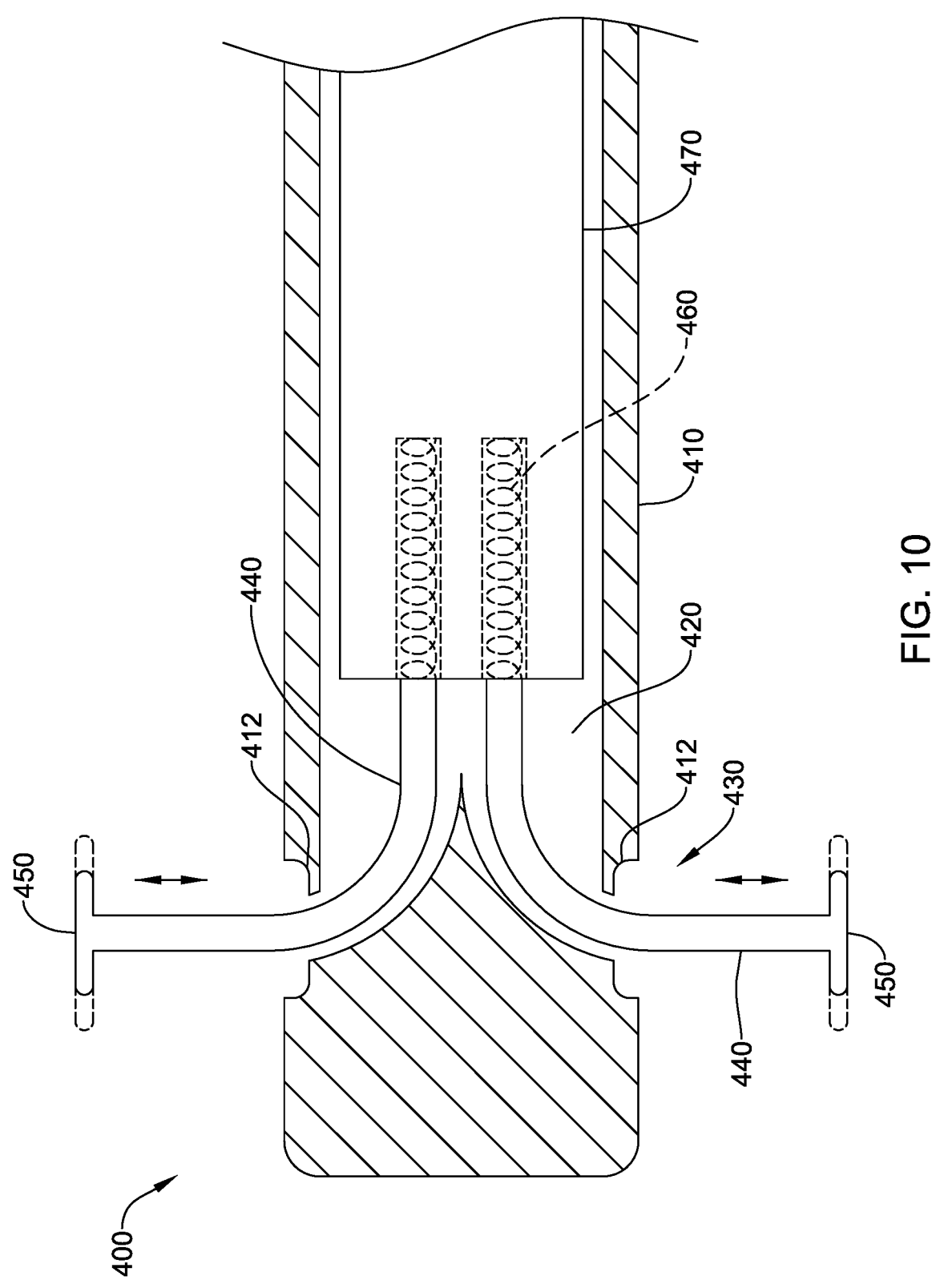

The plunger guide 430 may be configured to direct the plurality of plunger shafts 440 radially outward from the plunger guide 430 and/or the elongate sheath 410 as the plurality of plunger shafts 440 is advanced distally within the at least one lumen 420 and/or relative to the elongate sheath 410, as seen in FIG. 10. In some embodiments, the plunger guide 430 may include a plurality of conduits 432 formed therein. The plurality of conduits 432 may be in fluid communication with the at least one lumen 420. The plurality of plunger shafts 440 may be disposed within and/or may extend through the plurality of conduits 432.

In some embodiments, hydraulic pressure and/or a vacuum may be applied to the plurality of plunger shafts 440 to move and/or translate the plurality of plunger shafts 440 proximally and/or distally. In some embodiments, hydraulic pressure may be applied to the plurality of plunger shafts 440 to change physical characteristics and/or properties (e.g., stiffness, column strength, flexibility, etc.) of the plurality of plunger shafts 440. In some embodiments, hydraulic pressure may be applied to the plurality of plunger shafts 440 to direct and/or steer one or more segments and/or portions of the plurality of plunger shafts 440. In some embodiments, hydraulic pressure may be applied to the plurality of plunger shafts 440 to direct and/or steer one or more segments and/or portions of the plurality of plunger shafts 440 utilizing semi-compliant polymers for shaft wall materials. Other configurations are also contemplated.

In some embodiments, at least one plunger shaft of the plurality of plunger shafts 440 may include an implant interface element 450 at a distalmost end thereof. In at least some embodiments, the implant interface element 450 may have a generally flattened configuration and/or may form a plate-like structure. In some embodiments, the implant interface element 450 may be substantially rigid to resist deflection when applying force to a medical implant. In some embodiments, the implant interface element 450 may be semi-flexible and may resist significant deflection while permitting a small amount of deflection and/or flexibility to reduce the possibility of damage to the medical implant.

In some embodiments, one or more sections and/or portions of the at least one plunger shaft may be formed from a durable shape memory alloy which may maintain useful column strength to push and flex in segments. In some embodiments, one or more sections and/or segments of the at least one plunger shaft may vary in properties proximal to distal.

In at least some embodiments, the elongate sheath 410 may include a plurality of recesses 412 corresponding to and/or configured to receive the implant interface element(s) 450. In some embodiments, when the implant interface element 450 is received within the plurality of recesses 412, a distal surface of the implant interface element 450 may be substantially parallel to and/or substantially flush with an outer surface of the elongate sheath 410. Other configurations are also contemplated.

In some embodiments, the implant interface element 450 may be expandable outward from its respective plunger shaft. In some embodiments, the implant interface element 450 may be inflatable and/or expandable when filled with an inflation fluid delivered through a lumen formed in its respective plunger shaft. In some embodiments, the implant interface element 450 may be formed from a shape memory material that is configured to expand in vivo (e.g., when subjected to internal body temperature). Other configurations are also contemplated.

In some embodiments, the elongate sheath 410 includes a main plunger shaft 470 disposed within the at least one lumen 420. In at least some embodiments, the main plunger shaft 470 may be slidably disposed within the at least one lumen 420. In some embodiments, each plunger shaft of the plurality of plunger shafts 440 may be operably engaged with the main plunger shaft 470. In some embodiments, axial translation of the main plunger shaft 470 within the at least one lumen 420 results in and/or causes corresponding axial translation of the plurality of plunger shafts 440 within the at least one lumen 420 and/or the plurality of conduits 432.

In some embodiments, each plunger shaft of the plurality of plunger shafts 440 is engaged with a compression spring 460. In some embodiments, the compression spring 460 may be disposed within a recess or cavity formed in the main plunger shaft 470. In some embodiments, the compression spring 460 may be disposed axially between the main plunger shaft 470 and the plurality of plunger shafts 440. In some embodiments, the compression spring 460 may be disposed at proximal ends of the plurality of plunger shafts 440. Other configurations, including combinations thereof, are also contemplated.

In some embodiments, the compression spring 460 may permit axial movement of the plurality of plunger shafts 440 relative to the elongate sheath 410 and/or the main plunger shaft 470. By permitting independent movement of each plunger shaft of the plurality of plunger shafts 440, the implant remodeling tool 400 and/or the plurality of plunger shafts 440 may better conform to the shape the tissue in which the medical implant is disposed. The compression spring 460 may cooperate with axial movement of the plurality of plunger shafts 440 to apply outward radial force to the medical implant after it is deployed within the patient. In some embodiments, all plunger shafts of the plurality of plunger shafts 440 are engaged with a single compression spring. In some embodiments, each plunger shaft of the plurality of plunger shafts 440 is engaged with its own compression spring.

Figure 11:
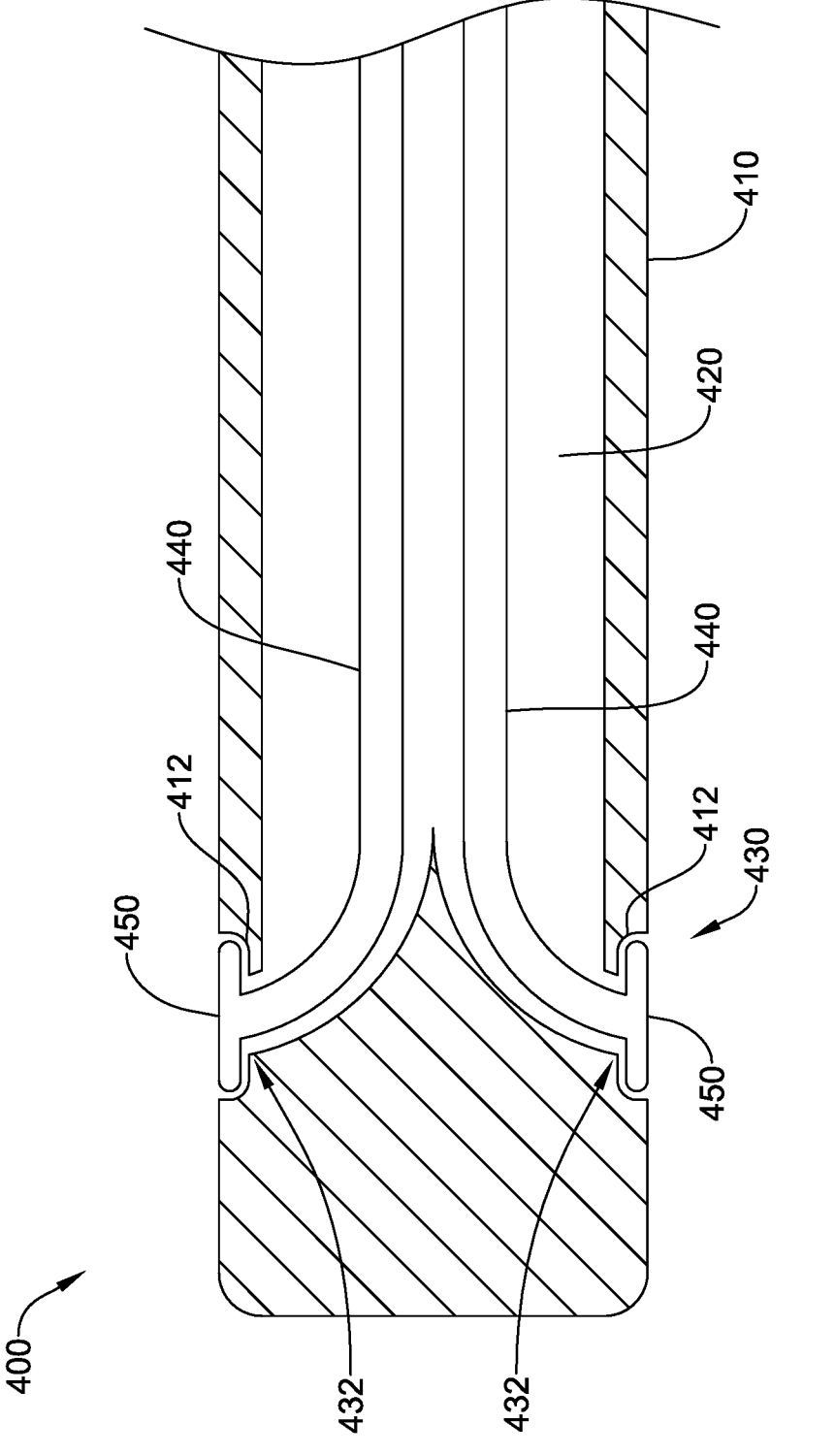
Figure 12:
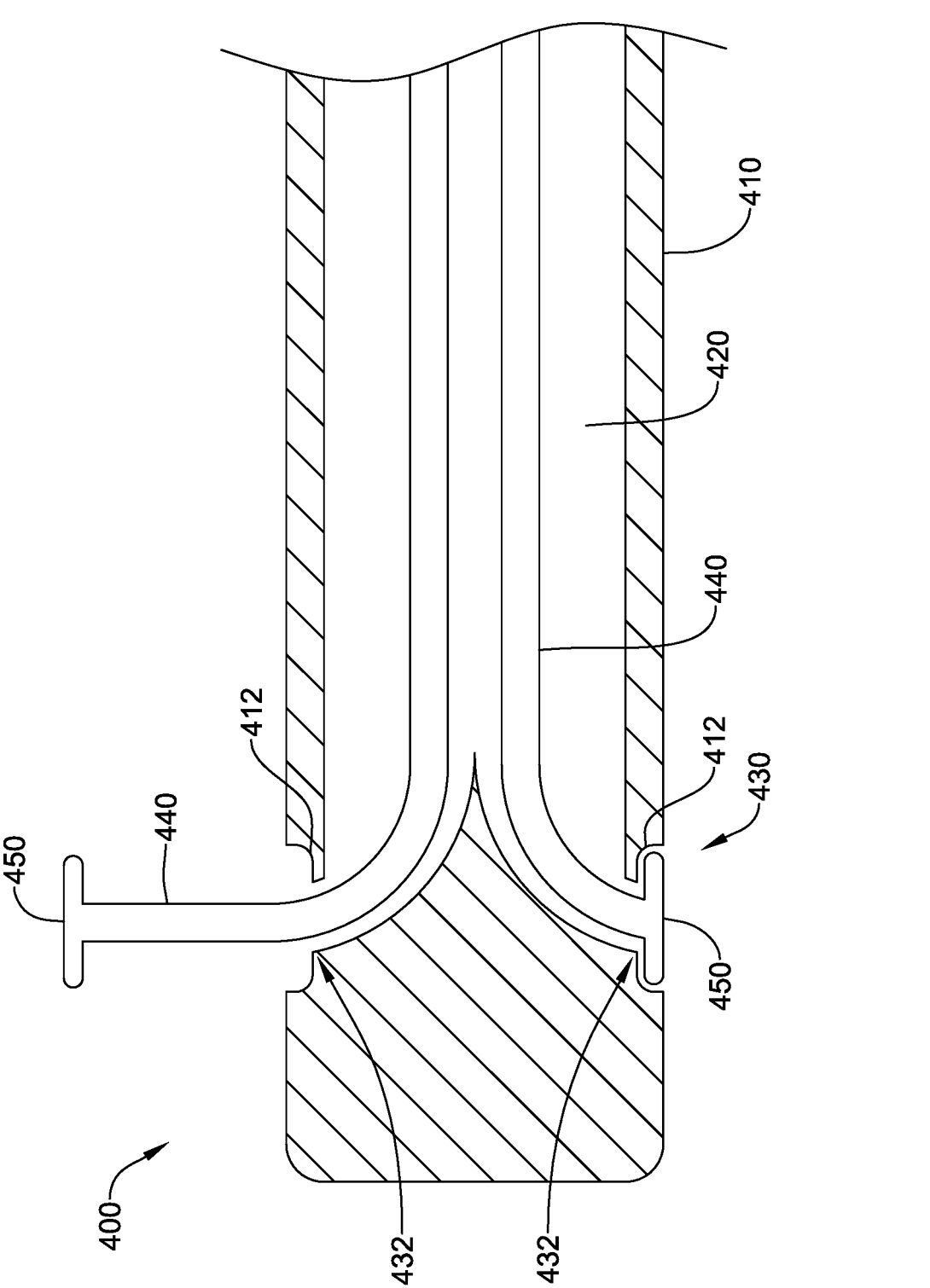

In some embodiments, the implant remodeling tool 400 and/or the elongate sheath 410 may be devoid of the main plunger shaft 470, as seen in FIG. 11. In some embodiments, each plunger shaft of the plurality of plunger shafts 440 may be axially translatable within the at least one lumen 420 and/or relative to the elongate sheath 410 completely independently of each other, as seen in FIG. 12.

In some embodiments, the compression spring 460 may be disposed within a proximal portion of the elongate sheath 410 and/or within a proximal handle of the elongate sheath 410. In some embodiments, the plurality of plunger shafts 440 may be configured for axial translation within the at least one lumen 420 and/or relative to the elongate sheath 410 in response to movement of the proximal handle and/or in response to an actuation mechanism. In some embodiments, the actuation mechanism may be disposed at and/or within the proximal portion of the elongate sheath 410 and/or the proximal handle. In some embodiments, the actuation mechanism may include manual mechanical control, electromechanical control, and/or hydraulic and/or vacuum controls. Other configurations are also contemplated.

Figure 13:
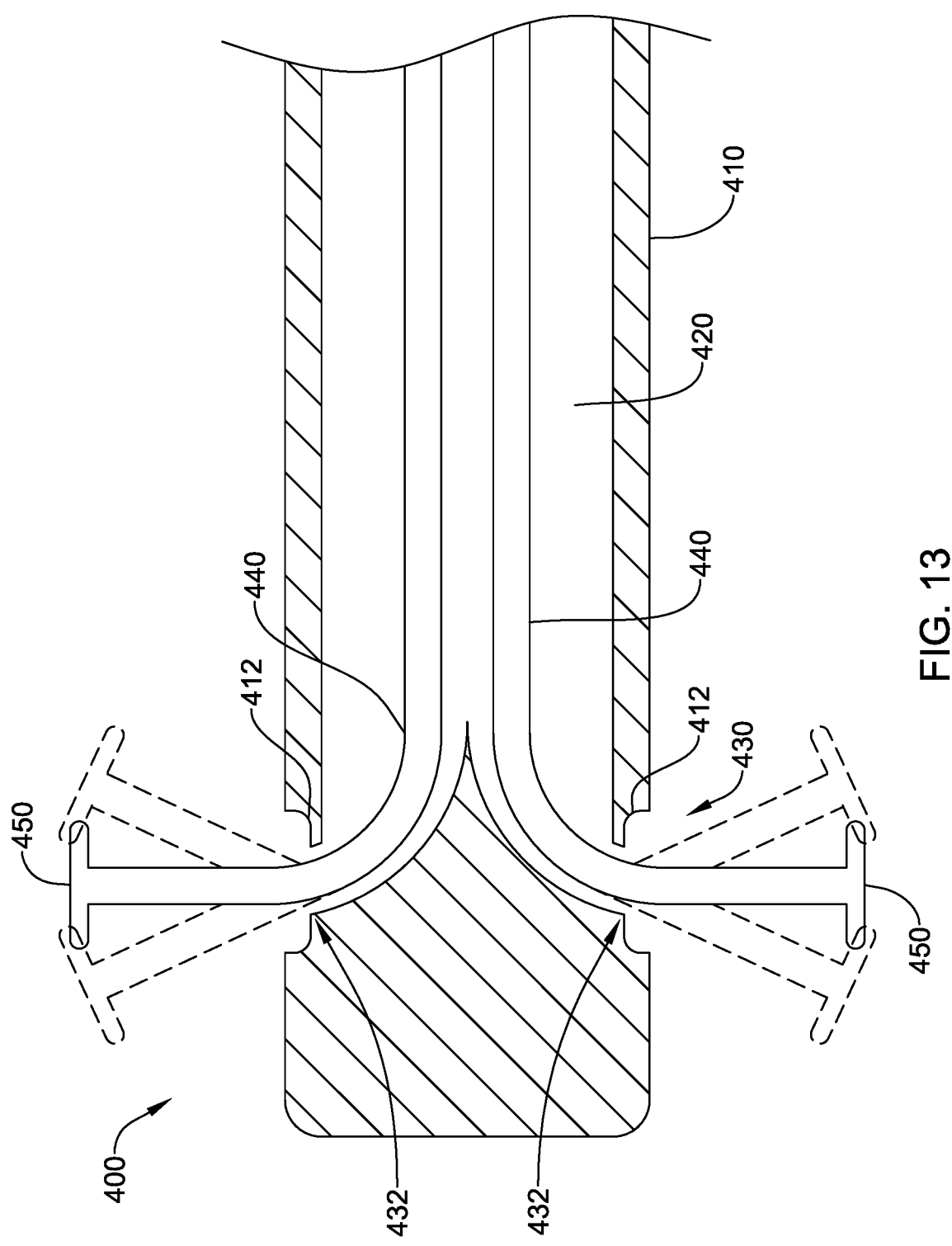

In some embodiments, the plurality of plunger shafts 440 may be steerable, as shown in FIG. 13. In some embodiments, at least one plunger shaft of the plurality of plunger shafts 440 may be steerable independently of any other plunger shafts of the plurality of plunger shafts 440. Steerability of the plurality of plunger shafts 440 may permit non-planar use of the plurality of plunger shafts 440 and/or may permit improved function of the implant remodeling tool 400 and/or the plurality of plunger shafts 440 while reducing movement of the implant remodeling tool 400 and/or the elongate sheath 410 in vivo.

Figure 14:
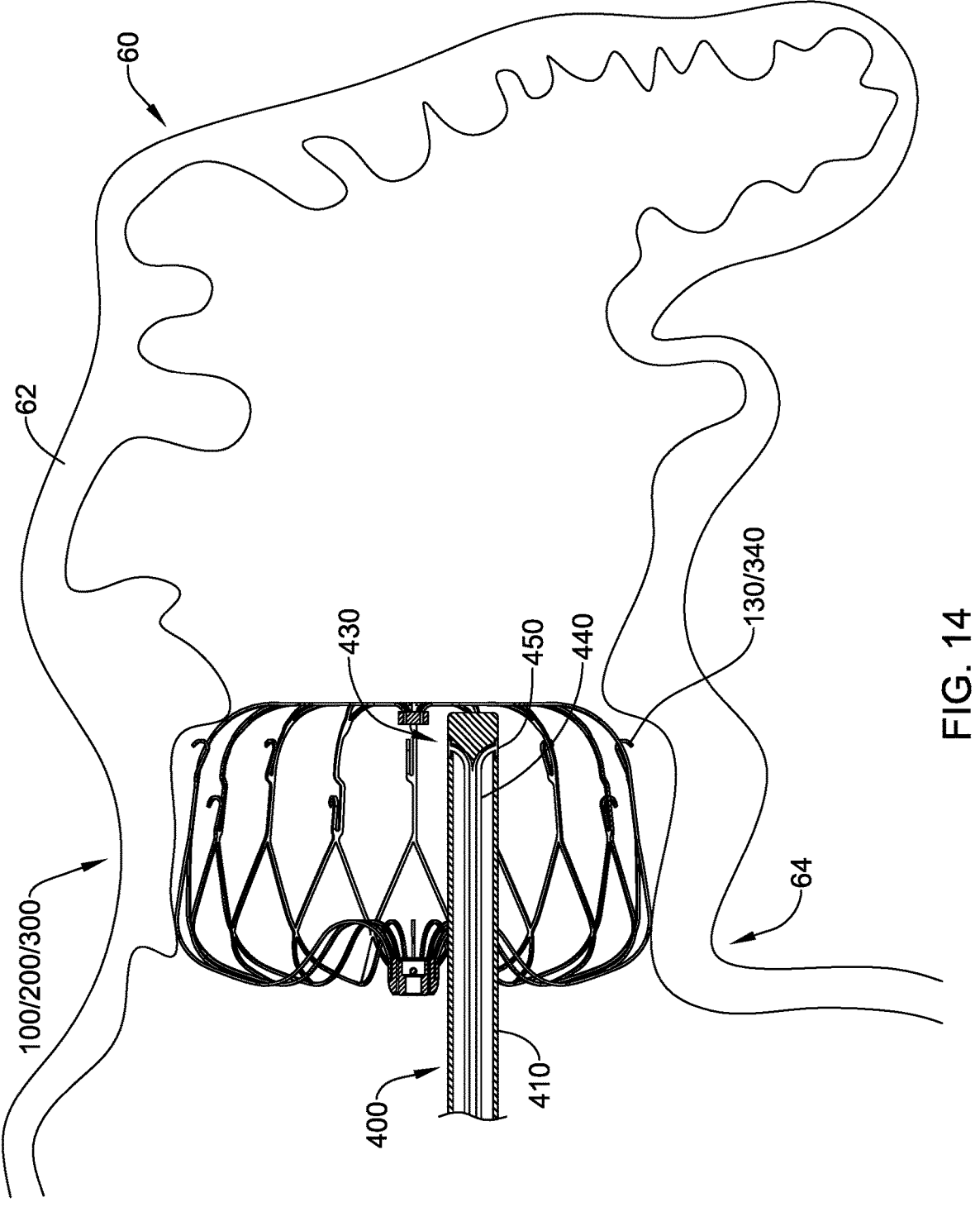
FIGS. 14-15 illustrate selected aspects of using the implant remodeling tool of FIGS. 9-13 to remodel a medical implant.
Figure 15:
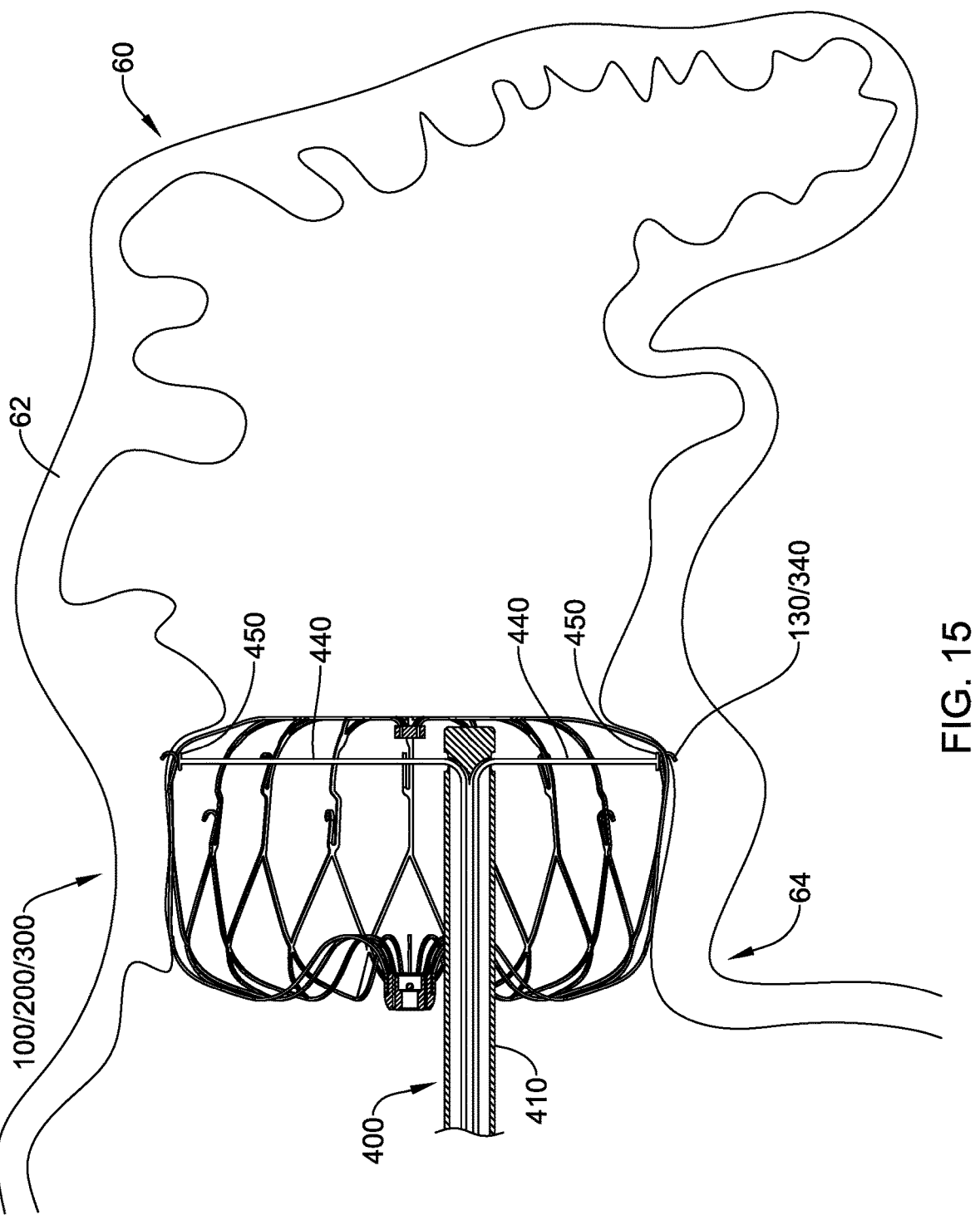

FIGS. 14-15 illustrate selected aspects of the implant remodeling tool 400 in use. As illustrated a medical implant 100 (which may include the occlusive implant 200/300) has been deployed within the left atrial appendage 60. For the purpose of illustration only, the medical implant 100 is shown in the left atrial appendage 60 in FIGS. 14-15, but other medical implants (such as the occlusive implant 200/300) and/or other body lumens may also be used in accordance with the disclosure.

As shown in FIG. 14, the medical implant 100 and/or the occlusive implant 200/300 may not fully engage the wall 62 of the left atrial appendage 60 when deployed adjacent the ostium 64 due to the irregular nature of the wall 62. In some cases, one or more portions of the medical implant 100 and/or the occlusive implant 200/300 may be spaced apart from the wall 62 of the left atrial appendage 60 after deployment, which may result in one or more of the plurality of anchor members 130/340 being disengaged from the wall 62 of the left atrial appendage 60 and failing to meaningfully contribute to anchoring the medical implant 100 and/or the occlusive implant 200/300 in place.

The elongate sheath 410 of the implant remodeling tool 400 may be inserted into an interior of the medical implant 100 and/or the occlusive implant 200/300, as shown in FIG. 14. In some embodiments, the elongate sheath 410 may be configured to be inserted through a proximal hub of the medical implant 100 and/or the occlusive implant 200/300. In some embodiments, the elongate sheath 410 may be configured to be inserted alongside a proximal hub of the medical implant 100 and/or the occlusive implant 200/300. Other configurations are also contemplated. The distal end of the elongate sheath 410 and/or the plunger guide 430 may be positioned within the medical implant 100 and/or the occlusive implant 200/300 such that the plurality of plunger shafts 440 and/or the implant interface element(s) 450 are positioned within reach of the plurality of anchor members 130/340.

The plurality of plunger shafts 440 may be advanced distally relative to the elongate sheath 410 and directed toward the plurality of anchor members 130/340 by the plurality of conduits 432 (e.g., FIGS. 9-13) of the plunger guide 430. In some embodiments, the plurality of plunger shafts 440 may be steered toward the plurality of anchor members 130/340. In some embodiments, the plurality of plunger shafts 440 and/or the implant interface element(s) 450 may be configured to engage the medical implant 100 and/or the occlusive implant 200/300 and urge at least a portion of the medical implant 100 and/or the occlusive implant 200/300 radially outward from the elongate sheath 410 and/or toward the wall 62 of the left atrial appendage 60, as shown in FIG. 15. In some embodiments, the plurality of plunger shafts 440 and/or the implant interface element(s) 450 may be configured to engage the medical implant 100 and/or the occlusive implant 200/300 and urge at least one of the plurality of anchor members 130/340 radially outward from the elongate sheath 410 and/or toward the wall 62 of the left atrial appendage 60. In some embodiments, the plurality of plunger shafts 440 may be configured to apply a radially outward force against the medical implant 100 and/or the occlusive implant 200/300 to improve apposition of the medical implant 100 and/or the occlusive implant 200/300 with the wall 62 of the left atrial appendage 60. In some embodiments, the plurality of plunger shafts 440 may be configured to apply a radially outward force against at least one of the plurality of anchor members 130/340 to improve engagement of the at least one of the plurality of anchor members 130/340 with the wall 62 of the left atrial appendage 60.

In some embodiments, the plurality of plunger shafts 440 may extend radially outward different lengths and/or distances from the elongate sheath 410 and/or the plunger guide 430 to accommodate positioning of the implant remodeling tool 400 within the interior of the medical implant 100 and/or the occlusive implant 200/300 and/or to accommodate variations and/or different shapes in the surrounding tissue (e.g., the wall 62 of the left atrial appendage 60). In some embodiments, the plurality of plunger shafts 440 may extend radially outward at different angles from the elongate sheath 410 and/or the plunger guide 430 to accommodate positioning of the implant remodeling tool 400 within the interior of the medical implant 100 and/or the occlusive implant 200/300 and/or to accommodate variations and/or different shapes in the surrounding tissue (e.g., the wall 62 of the left atrial appendage 60). Other configurations, including combinations thereof, are also contemplated.

In at least some embodiments, the implant remodeling tool 400 may be used multiple times and/or at multiple discrete locations within the medical implant 100 and/or the occlusive implant 200/300. In some embodiments, with appropriate sterilization procedures, the implant remodeling tool 400 may be reusable. In some embodiments, the implant remodeling tool 400 may be disposable and/or a single-use item.

Figure 16:
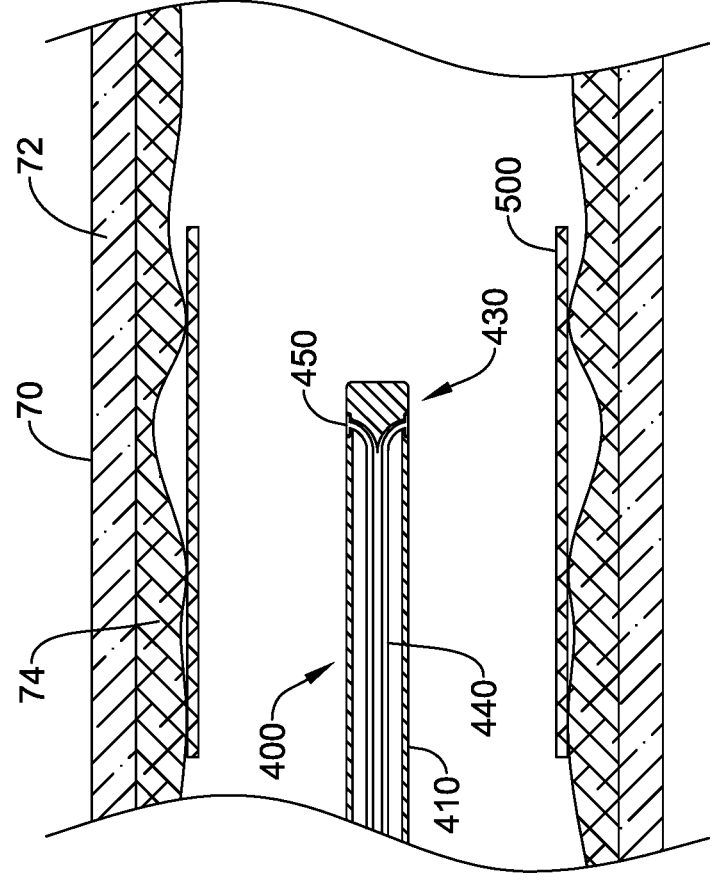
FIGS. 16-17 illustrate selected aspects of using the implant remodeling tool of FIGS. 9-13 to remodel a stent.
Figure 17:
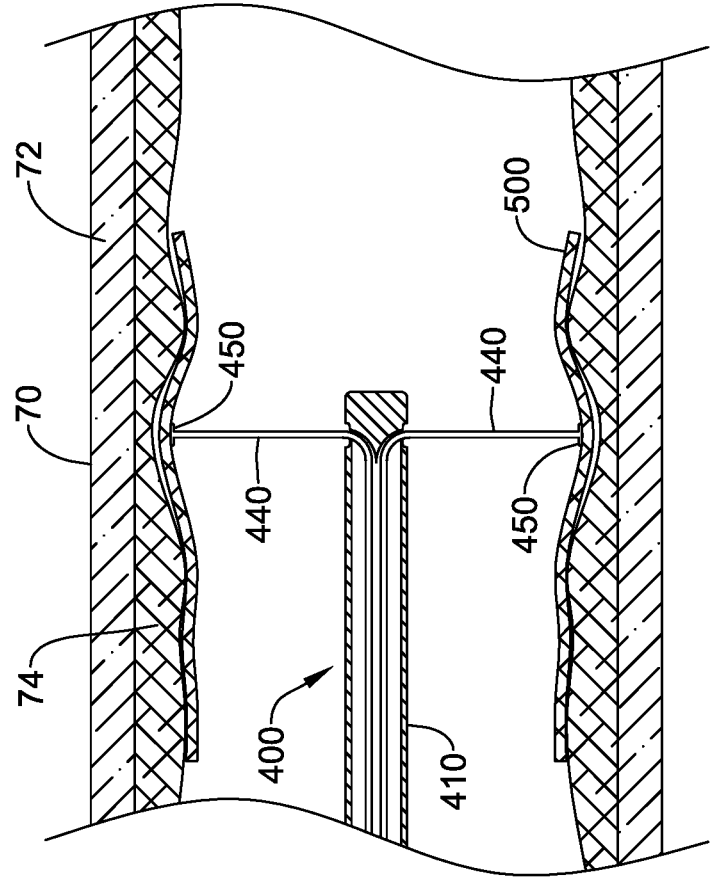

As discussed herein, in some embodiments, the implant remodeling tool 400 may be used with other types of medical implants and/or in other body lumens. FIGS. 16-17 illustrate a stent 500 disposed within a body lumen 70 having a wall 72. It will be appreciated that the stent 500 may be one of a variety of different types of stents, including but not limited to a stent or framework associated with a replacement heart valve implant.

In some embodiments, the body lumen 70 may have a stricture 74 disposed along an inner surface of the wall 72, treatment of which may include deploying the stent 500 therein. In some cases and/or with some types of stents, the stent 500 may be substantially rigid and/or may not conform well to an uneven inner surface of the stricture 74 after deployment and/or expansion of the stent 500, as seen in FIG. 16.

The elongate sheath 410 of the implant remodeling tool 400 may be inserted into an interior of the stent 500, as shown in FIG. 16. The distal end of the elongate sheath 410 and/or the plunger guide 430 may be positioned within the stent 500 such that the plurality of plunger shafts 440 and/or the implant interface element(s) 450 are positioned within and/or adjacent to portions of the stent 500 that are spaced apart radially inward from the wall 72 of the body lumen 70 and/or the stricture 74 disposed therein.

The plurality of plunger shafts 440 may be advanced distally relative to the elongate sheath 410 and directed toward the stent 500 by the plurality of conduits 432 (e.g., FIGS. 9-13) of the plunger guide 430. In some embodiments, the plurality of plunger shafts 440 may be steered toward the stent 500. In some embodiments, the plurality of plunger shafts 440 and/or the implant interface element(s)

450 may be configured to engage the stent 500 and urge at least a portion of the stent 500 radially outward from the elongate sheath 410 and/or toward the wall 72 of the body lumen 70 and/or the stricture 74, as shown in FIG. 17. In some embodiments, the plurality of plunger shafts 440 may be configured to apply a radially outward force against the stent 500 to improve apposition of the stent 500 with the wall 72 of the body lumen 70 and/or the stricture 74.

In some embodiments, the plurality of plunger shafts 440 may extend radially outward different lengths and/or distances from the elongate sheath 410 and/or the plunger guide 430 to accommodate positioning of the implant remodeling tool 400 within the interior of the stent 500 and/or to accommodate variations and/or different shapes in the surrounding tissue (e.g., the wall 72 of the body lumen 70 and/or the stricture 74). In some embodiments, the plurality of plunger shafts 440 may extend radially outward at different angles from the elongate sheath 410 and/or the plunger guide 430 to accommodate positioning of the implant remodeling tool 400 within the interior of the stent 500 and/or to accommodate variations and/or different shapes in the surrounding tissue (e.g., the wall 72 of the body lumen 70 and/or the stricture 74). Other configurations, including combinations thereof, are also contemplated. In at least some embodiments, the implant remodeling tool 400 may be used multiple times and/or at multiple discrete locations within the stent 500.

In some embodiments, a kit according to the disclosure may include the delivery sheath 40, and/or the medical device system 10 described herein, configured to deploy the medical implant 100 and/or the occlusive implant 200/300 (or another medical implant, such as the stent 500) at a treatment site, wherein the medical implant 100 and/or the occlusive implant 200/300 (or another medical implant, such as the stent 500) is configured to shift from a delivery configuration toward and/or to a deployed configuration upon release from the delivery sheath 40. The kit according to the disclosure may include the implant remodeling tool 400 discussed herein, wherein the implant remodeling tool 400 is configured to improve engagement of the medical implant 100 and/or the occlusive implant 200/300 (or another medical implant, such as the stent 500) with adjacent tissue at the treatment site. In some embodiments, the kit according to the disclosure, including the delivery sheath 40 (and/or the medical device system 10), with or without the associated medical implant, and the implant remodeling tool 400, may be packaged together for use during a single procedure. Other configurations are also contemplated.

The materials that can be used for the various components of the medical implants, systems, and methods of manufacturing disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the central hub, the plurality of elongate members, the occlusive element, the elongate sheath, the plurality of plunger shafts, the plunger guide, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane, polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In some embodiments, portions or all of the system and/or components thereof may be doped with, made of, or otherwise include a radiopaque material. Radiopaque materials are understood to be materials capable of producing a relatively bright image on a fluoroscopy screen or another imaging technique (e.g., ultrasound, etc.) during a medical procedure. This relatively bright image aids a user in determining the location of the system. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene tere-phthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. In some embodiments, the yarns may be made from thermo-plastic materials including, but not limited to, polyesters, polypropylenes, polyethylenes, polyurethanes, polynaphtha-lenes, polytetrafluoroethylenes, and the like. The yarns may be of the multifilament, monofilament, or spun types. The type and denier of the yarn chosen may be selected in a manner which forms a biocompatible system.

In some embodiments, the system and/or other elements disclosed herein may include and/or be treated with a suitable therapeutic agent. Some examples of suitable thera-peutic agents may include anti-thrombogenic agents (such as heparin, heparin derivatives, urokinase, and PPack (dextro-phenylalanine proline arginine chloromethyl ketone)); anti-protein and/or anti-bacterial agents (such as 2-methacryroy-loxyethyl phosphorylcholine (MPC) and its polymers or copolymers); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasa-lazine, and mesalamine); antineoplastic/antiproliferative/anti-mitotic agents (such as paclitaxel, 5-fluorouracil, cis-platin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antago-nists, transcriptional activators, and translational promot-ers); vascular cell growth inhibitors (such as growth factor inhibitors, growth factor receptor antagonists, transcrip-tional repressors, translational repressors, replication inhibi-tors, inhibitory antibodies, antibodies directed against growth factors, bifunctional molecules consisting of a growth factor and a cytotoxin, bifunctional molecules con-sisting of an antibody and a cytotoxin); immunosuppressants (such as the "olimus" family of drugs, rapamycin analogues, macrolide antibiotics, biolimus, everolimus, zotarolimus, temsirolimus, picrolimus, novolimus, myolimus, tacrolimus, sirolimus, pimecrolimus, etc.); cholesterol-lowering agents; vasodilating agents; and agents which interfere with endog-enous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An implant remodeling tool configured to improve engagement of a medical implant with adjacent tissue, comprising:

an elongate sheath having at least one lumen extending therein, and a plunger guide disposed proximate a distal end of the elongate sheath; and a plurality of plunger shafts extending from the at least one lumen through the plunger guide;

wherein the plunger guide is configured to direct the plurality of plunger shafts radially outward from the plunger guide as the plurality of plunger shafts is advanced distally;

wherein the plurality of plunger shafts is configured to engage the medical implant and urge at least a portion of the medical implant radially outward from the elon-gate sheath.

2. The implant remodeling tool of claim 1, wherein at least one plunger shaft of the plurality of plunger shafts includes an implant interface element at a distalmost end thereof.

3. The implant remodeling tool of claim 1, wherein each plunger shaft of the plurality of plunger shafts is engaged with a compression spring.

4. The implant remodeling tool of claim 3, wherein each plunger shaft of the plurality of plunger shafts is engaged with its own compression spring.

5. The implant remodeling tool of claim 1, wherein the elongate sheath includes a main plunger shaft disposed within the at least one lumen;

wherein each plunger shaft of the plurality of plunger shafts is operably engaged with the main plunger shaft.

6. The implant remodeling tool of claim 1, wherein each plunger shaft of the plurality of plunger shafts is axially translatable independently of each other.

7. The implant remodeling tool of claim 1, wherein at least one plunger shaft of the plurality of plunger shafts is steerable independently of any other plunger shafts of the plurality of plunger shafts.

8. A kit, comprising:

a delivery sheath configured to deploy a medical implant at a treatment site, wherein the medical implant is configured to shift from a delivery configuration toward a deployed configuration upon release from the deliv-ery sheath; and an implant remodeling tool configured to improve engagement of the medical implant with adjacent tissue at the treatment site;

wherein the implant remodeling tool includes:

an elongate sheath having at least one lumen extending therein, and a plunger guide disposed proximate a distal end of the elongate sheath; and a plurality of plunger shafts extending from the at least one lumen through the plunger guide;

wherein the plunger guide is configured to direct the plurality of plunger shafts radially outward from the plunger guide as the plurality of plunger shafts is advanced distally;

wherein the plurality of plunger shafts is configured to engage the medical implant and urge at least a portion of the medical implant radially outward from the elongate sheath and into engagement with adjacent tissue at the treatment site.

* * * * *